(12) United States Patent
Oike et al.

(10) Patent No.: US 8,780,194 B2
(45) Date of Patent: Jul. 15, 2014

(54) COMPONENT PRESENCE/ABSENCE JUDGING APPARATUS AND METHOD

(75) Inventors: Hiroshi Oike, Chiryu (JP); Ikuo Suzuki, Chiryu (JP)

(73) Assignee: Fuji Machine Mfg. Co., Ltd., Chiryu-shi (JP)

( * ) Notice: Subject to any disclaimer, the term of this patent is extended or adjusted under 35 U.S.C. 154(b) by 412 days.

(21) Appl. No.: 13/179,745

(22) Filed: Jul. 11, 2011

(65) Prior Publication Data

US 2012/0013731 A1 Jan. 19, 2012

(30) Foreign Application Priority Data

Jul. 13, 2010 (JP) ................................. 2010-159073
Jun. 30, 2011 (JP) ................................. 2011-146593

(51) Int. Cl.
*H04N 9/47* (2006.01)

(52) U.S. Cl.
USPC ............................................................ 348/87

(58) Field of Classification Search
USPC ............................................................ 348/87
See application file for complete search history.

(56) References Cited

U.S. PATENT DOCUMENTS

| | | | | |
|---|---|---|---|---|
| 5,249,349 | A * | 10/1993 | Kuinose et al. ................. | 29/721 |
| 2003/0072044 | A1* | 4/2003 | Hashiguchi et al. .......... | 358/520 |
| 2006/0140471 | A1* | 6/2006 | Murakami et al. ............ | 382/145 |
| 2008/0068593 | A1* | 3/2008 | Nakano et al. .................. | 356/73 |
| 2009/0115718 | A1* | 5/2009 | Qiao et al. ..................... | 345/102 |

FOREIGN PATENT DOCUMENTS

JP 2001-345600 12/2001

OTHER PUBLICATIONS

U.S. Appl. No. 13/177,020, filed Jul. 6, 2011, Hiroshi Oike, et al.

* cited by examiner

*Primary Examiner* — Dave Czekaj
*Assistant Examiner* — Tracy Li
(74) *Attorney, Agent, or Firm* — Oblon, Spivak, McClelland, Maier & Neustadt, L.L.P.

(57) ABSTRACT

A component presence/absence judging apparatus judges the presence/absence of a component through a registration step and an inspection step. The registration step comprises an ante-mounting color information acquisition step, a post-mounting color information acquisition step and an inspection area determination step. Ante-mounting color information is acquired from an ante-mounting image taken at a predetermined portion on an ante-mounting board. Post-mounting color information is acquired from a post-mounting image taken at the predetermined portion on a post-mounting board. Then, a section having a large difference between both color information of the ante-mounting image and the post-mounting image is identified and is determined as an inspection area. At the inspection step, the presence/absence of the component at a predetermined place on each inspection board to be inspected is judged in dependence on the color information on the determined inspection area.

5 Claims, 8 Drawing Sheets

Processing Operation Flow Chart of Processing Unit 11

Flow Chart of Registration Step S1

Flow Chart of Ante-mounting Color Information Acquisition Step S10

Flow Chart of Storage Step S13

Flow Chart of Inspection Step S2

Flow Chart of Post-mounting Operation Color Information Acquisition Step S20

COMPONENT PRESENCE/ABSENCE JUDGING APPARATUS AND METHOD

INCORPORATION BY REFERENCE

This application is based on and claims priorities under 35 U.S.C. 119 with respect to Japanese patent applications No. 2010-159073 filed on Jul. 13, 2010 and No. 2011-146593 filed on Jun. 30, 2011, the entire contents of which are incorporated herein by reference.

BACKGROUND OF THE INVENTION

1. Field of the Invention

The present invention relates to a component presence/absence judging apparatus and a component presence/absence judging method for judging whether or not a components is mounted at a predetermined portion on a board after a component mounting operation.

2. Discussion of the Related Art

As component presence/absence judging apparatus and method for judging whether or not a component is mounted at a predetermined portion on a board after a component mounting operation, there have been known electronic component mounting confirmation equipment and method which are disclosed in, for example, JP2001-345600 A.

In the known equipment and method, there are detected a color indicating a scheduled mounting place on a board before the mounting of an electronic component and another color indicating the scheduled mounting place on the board after the mounting of the electronic component, and these colors detected are compared to confirm the mounting state of the electronic component at the scheduled mounting place on the board.

However, in the known equipment and method, it is carried out to detect the color at around the center part of the electronic component which part is drawn to a nozzle at the time of a mounting operation. Therefore, where the color at around the center part of the electronic component is a color which hardly differs from the color at the scheduled mounting place on the board for the mounting of the electronic component, there occurs a possibility that the component is erroneously judged not to be mounted thought having been mounted.

SUMMARY OF THE INVENTION

Accordingly, it is an object of the present invention to provide a component presence/absence judging apparatus and a component presence/absence judging method capable of accurately judging whether or not a component is mounted at a predetermined place on a board after the mounting of the component.

In order to solve the foregoing problem, as a result of engaging in enthusiastic study and repeating one trial and error after another, the present inventors reached completion of the present invention through a finding that it is possible to accurately judge whether or not a component is mounted at a predetermined place after the mounting of the component, by determining, from color information before and after the mounting, a section which has a large difference in color information before and after the mounting, as an inspection area, and then by judging the presence/absence of the component at the predetermined place in dependence on the color information on the determined inspection area.

Briefly, according to the present invention in a first aspect, there is provided a component presence/absence judging apparatus for judging whether or not a components is mounted at a predetermined place on a board after a component mounting operation which mounts the component on the board. The apparatus comprises an image pickup device for relatively moving the board and a camera to pickup an image of a predetermined portion on the board where the component is to be mounted; ante-mounting color information acquisition means for acquiring ante-mounting color information from an ante-mounting image which the camera picks up at the predetermined portion on an ante-mounting board before mounting the component at the predetermined place thereon; post-mounting color information acquisition means for acquiring post-mounting color information from a post-mounting image which the camera picks up at the predetermined portion on a post-mounting board after mounting the component at the predetermined place thereon; inspection area determination means for determining an inspection area by identifying a section having a large difference between the ante-mounting color information and the post-mounting color information; and storage means for storing, for each predetermined portion, the inspection area and the ante-mounting color information and the post-mounting color information in the inspection area. The apparatus further comprises post-mounting operation color information acquisition means for acquiring post-mounting operation color information from the inspection area on a post-mounting operation image which the camera picks up at the predetermined portion on an inspection board after a component mounting operation which mounts the component at the predetermined place thereon; and judgment means for judging whether or not the component is mounted at the predetermined place on the inspection board, by comparing the post-mounting operation color information with the ante-mounting color information and the post-mounting color information.

According to the present invention in a second aspect, there is provided a component presence/absence judging method for judging whether or not a component is mounted at a predetermined place on a board after a component mounting operation which mounts the component on the board. The method comprises an ante-mounting color information acquisition step of acquiring ante-mounting color information from an ante-mounting image which an image pickup device picks up at a predetermined portion, where the component is to be mounted, on an ante-mounting board before mounting the component at the predetermined place thereon; a post-mounting color information acquisition step of acquiring post-mounting color information from a post-mounting image which the image pickup device picks up at the predetermined portion on a post-mounting board after mounting the component at the predetermined place thereon; an inspection area determination step of determining an inspection area by identifying a section having a large difference between the ante-mounting color information and the post-mounting color information; and a storage step of storing, for each predetermined portion, the inspection area and the ante-mounting color information and the post-mounting color information in the inspection area. The method further comprises a post-mounting operation color information acquisition step of acquiring post-mounting operation color information from the inspection area on a post-mounting operation image which the camera picks up at the predetermined portion on an inspection board after a component mounting operation which mounts the component at the predetermined place thereon; and a judgment step of judging whether or not the component is mounted at the predetermined place on the inspection board, by comparing the post-mounting operation color information with the ante-mounting color information and the post-mounting color information.

With the construction in each of the first and second aspects, the section having a larger difference in color information between before and after the mounting of a component is determined as the inspection area. Then, whether or not the component is mounted is judged in dependence on the color information in the inspection area. Thus, judgment of whether or not the component is mounted can be made accurately in comparison with the prior art wherein such judgment is made in dependence on the color information at around the center part of a component.

BRIEF DESCRIPTION OF THE ACCOMPANYING DRAWINGS

The foregoing and other objects and many of the attendant advantages of the present invention may readily be appreciated as the same becomes better understood by reference to the preferred embodiment of the present invention when considered in connection with the accompanying drawings, wherein like reference numerals designate the same or corresponding parts throughout several views, and in which.

Figure 4:
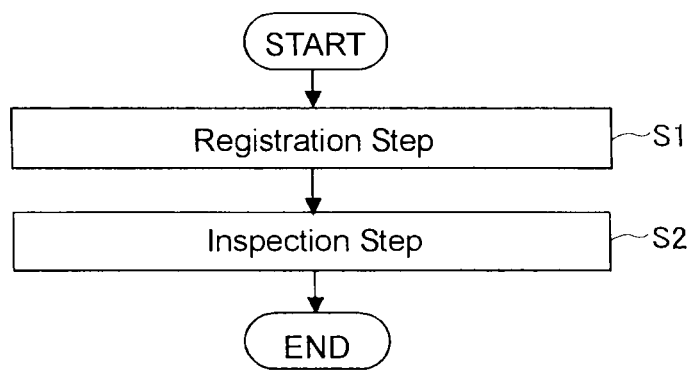
FIG. 4 is a flow chart showing a processing operation executed by a processing unit in FIG. 1.
Figure 5:
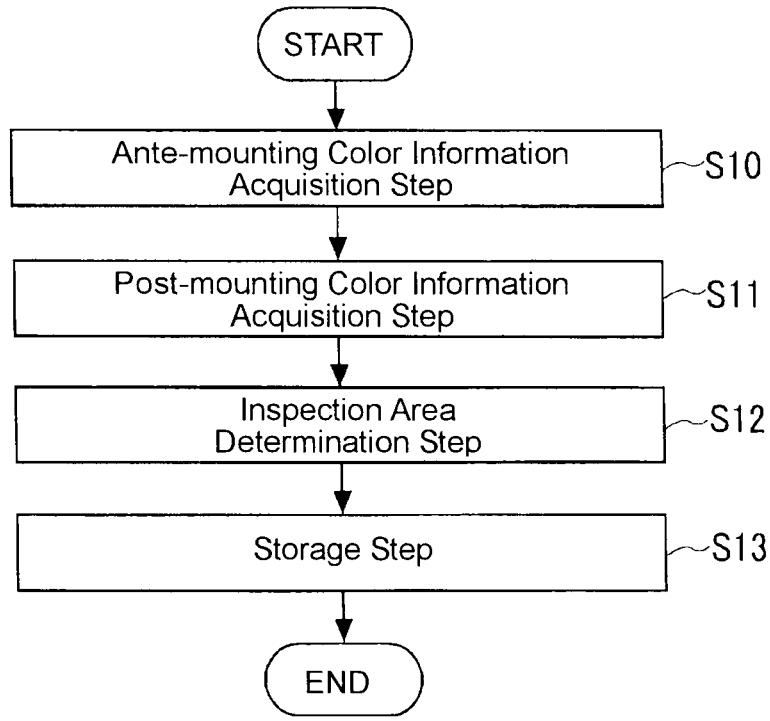
FIG. 5 is a flow chart showing a registration step in FIG. 4.
Figures 7A, 7B:
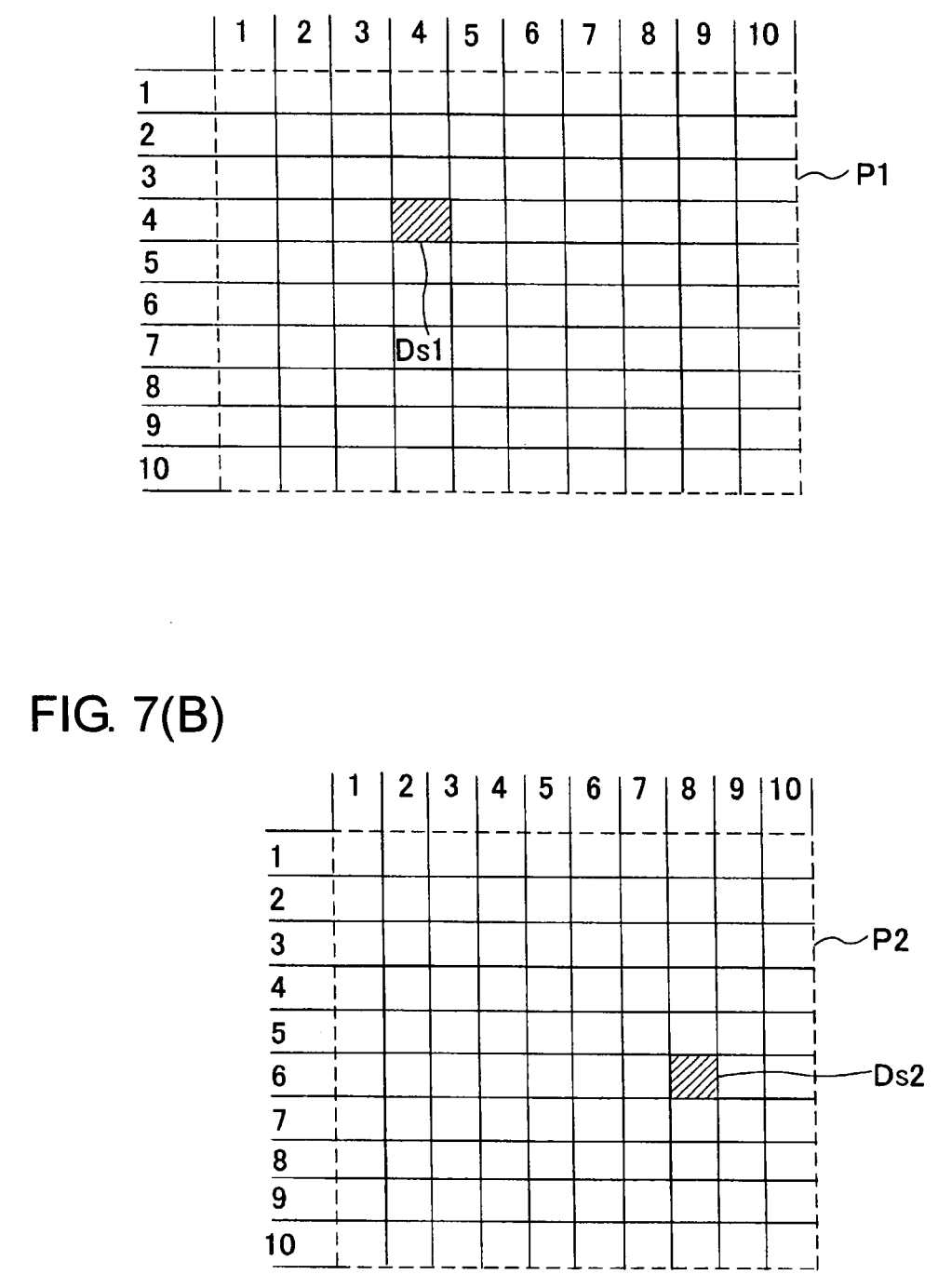
Figure 8:
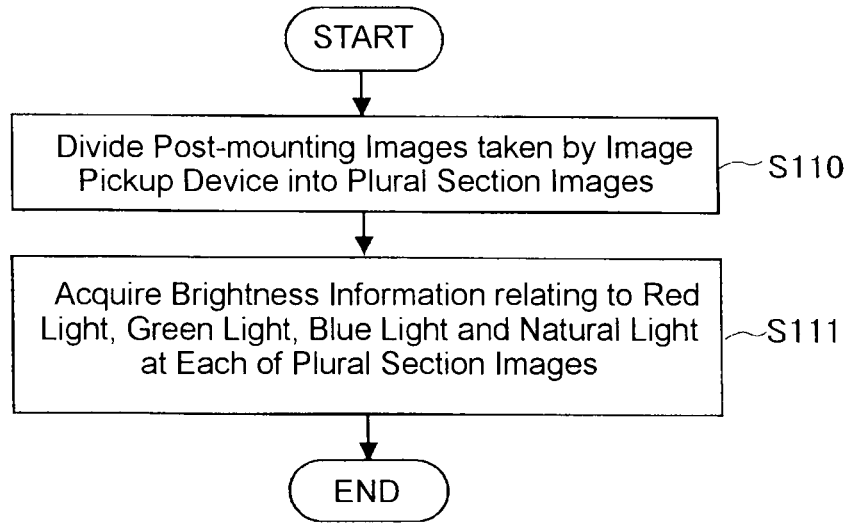
Figure 9:
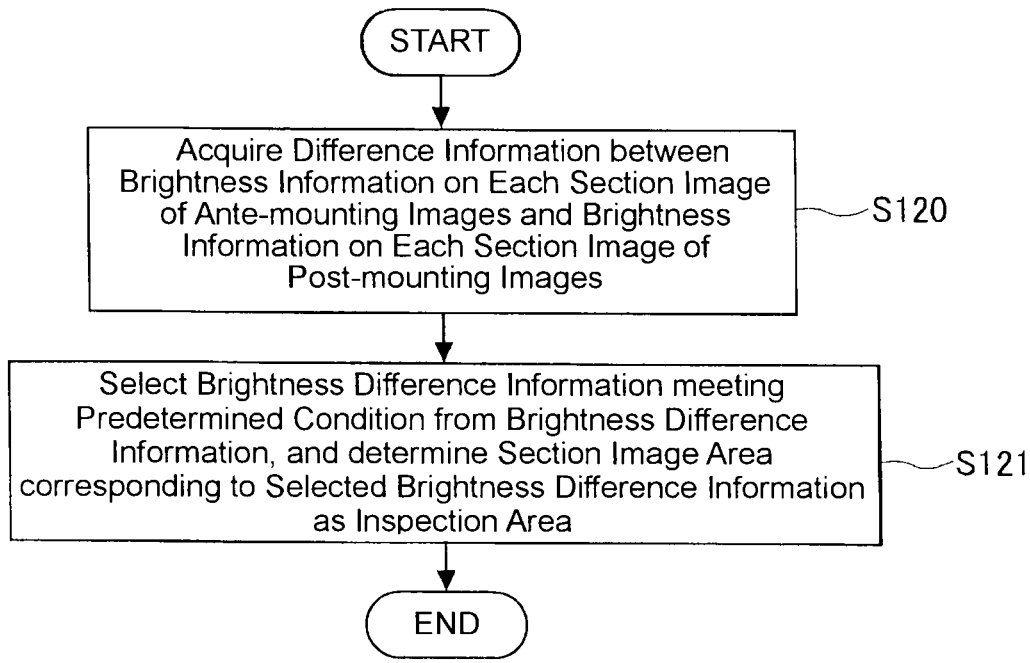
Figure 10:
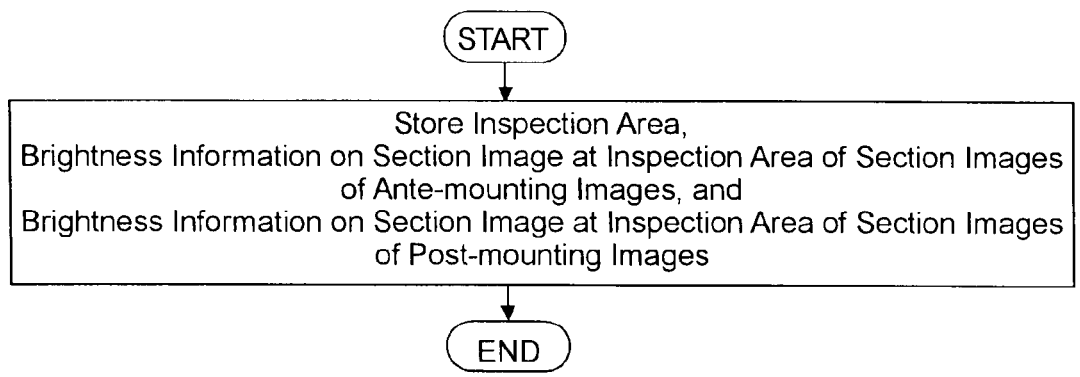
Figure 11:
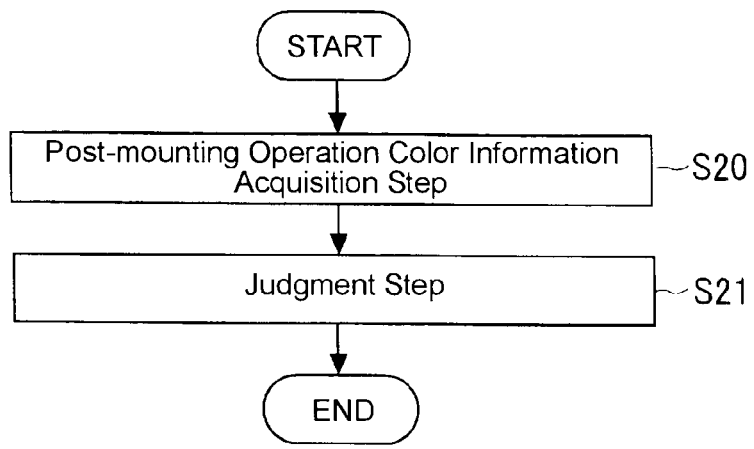
Figure 12:
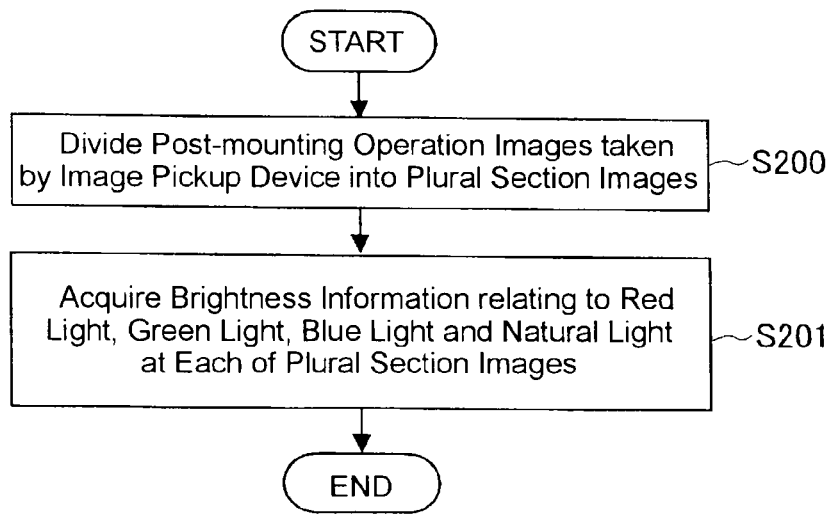
Figure 13:
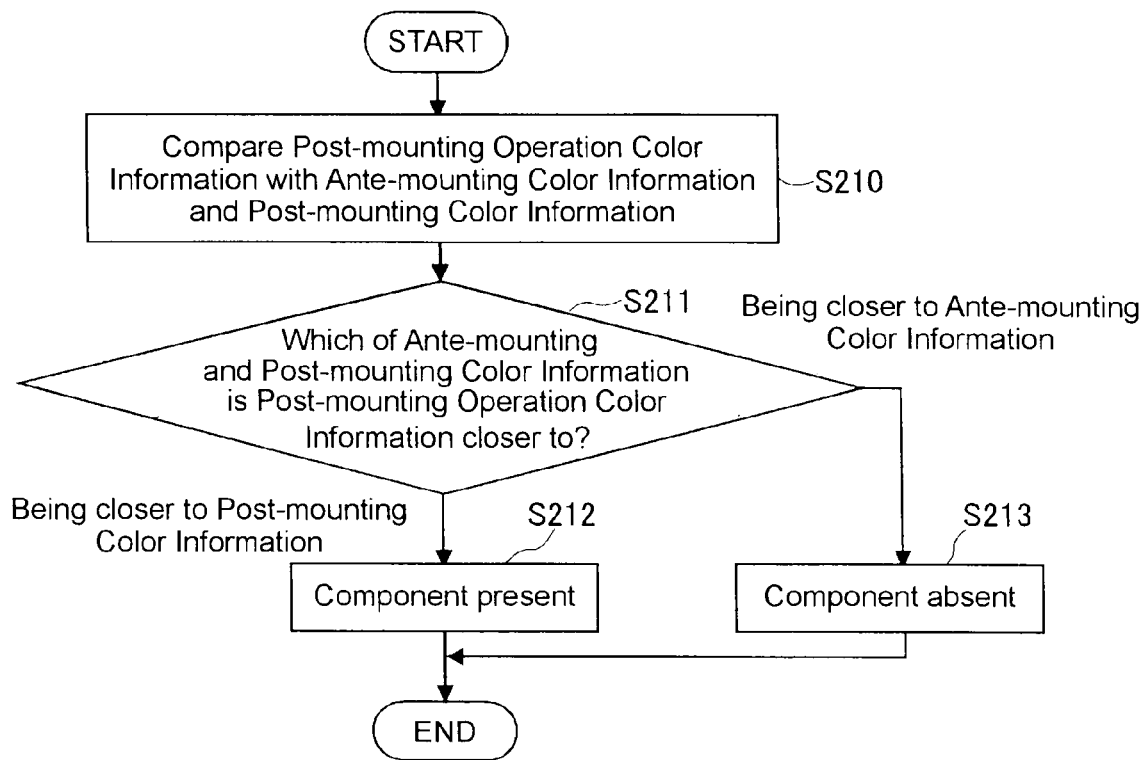

FIGS. 7(A) and 7(B) are explanatory views each for explaining divisions of section images at an image division step;

FIG. 8 is a flow chart showing a post-mounting color information acquisition step in FIG. 5;

FIG. 9 is a flow chart showing an inspection area determination step in FIG. 5;

FIG. 10 is a flow chart showing the detail of a storage step in FIG. 5;

FIG. 11 is a flow chart showing an inspection step in FIG. 4;

FIG. 12 is a flow chart showing a post-mounting operation color information acquisition step in FIG. 11; and FIG. 13 is a flow chart of a judgment step in FIG. 11.

DETAILED DESCRIPTION OF THE PREFERRED EMBODIMENT

Figure 1:
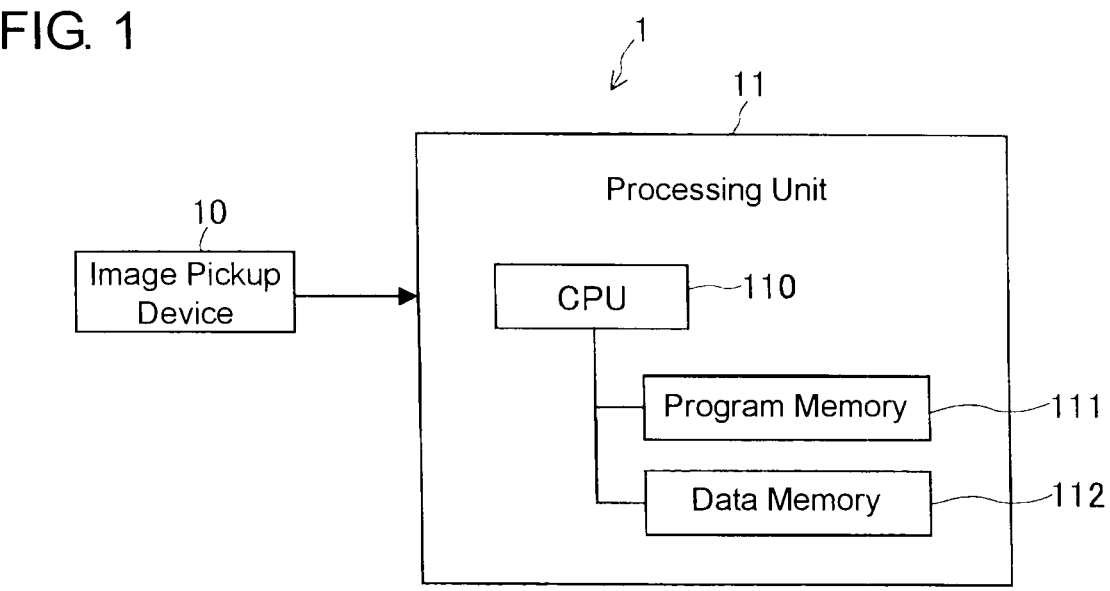
FIG. 1 is a block diagram of a component presence/absence judging apparatus for implementing a component presence/absence judging method in an embodiment according to the present invention.
Figure 2:
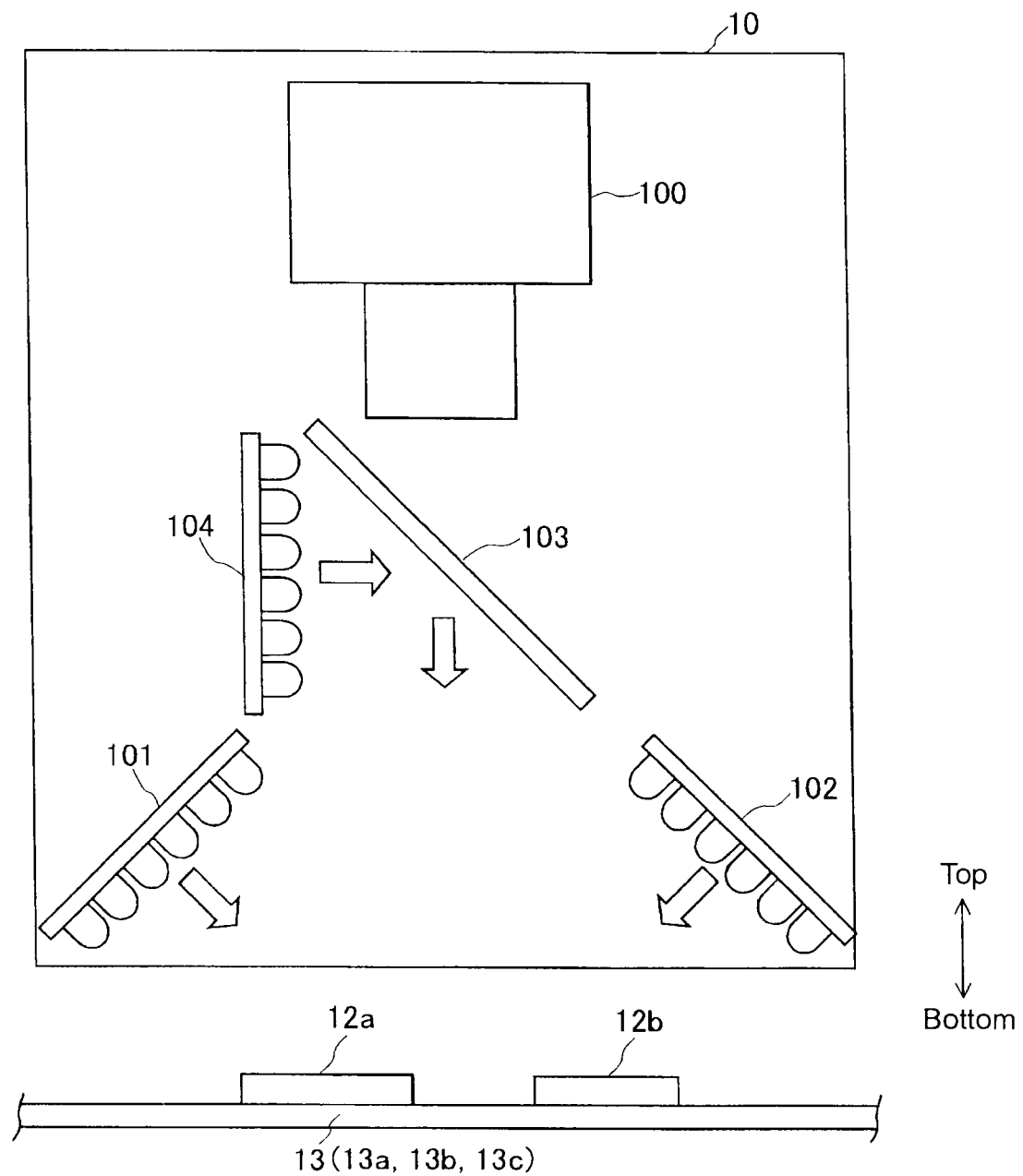
FIG. 2 is a schematic view of an image pickup device in FIG. 1.
Figure 3:
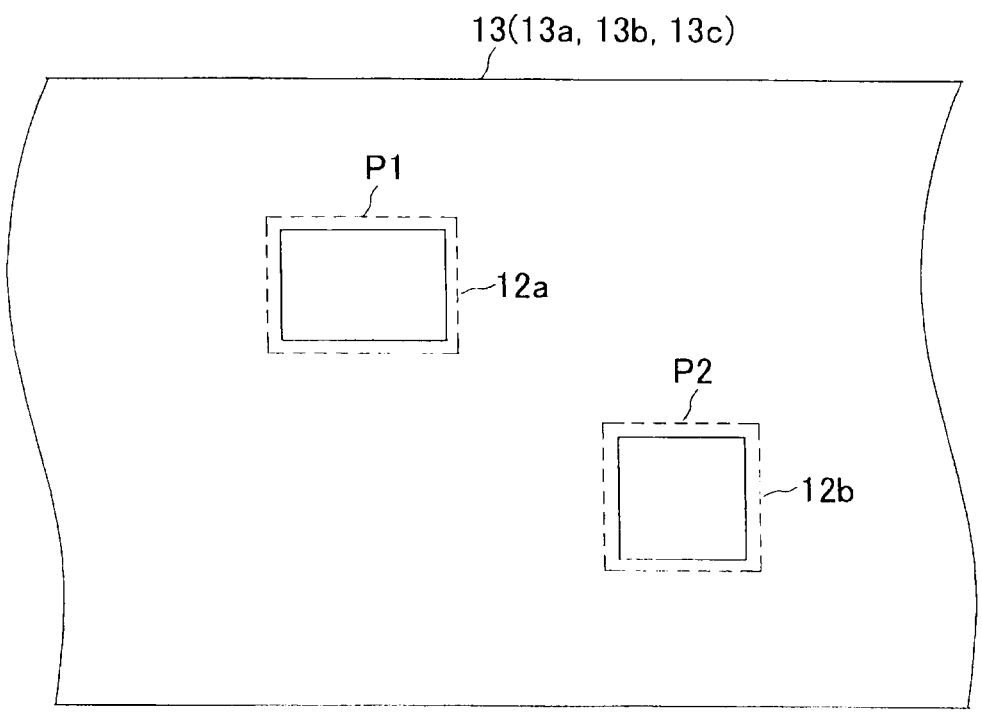
FIG. 3 is a plan view of a board.

Hereafter, an embodiment according to the present invention will be described with reference to the accompanying drawings. First of all, with reference to FIGS. 1 through 3, the construction of a component presence/absence judging apparatus will be described together with a component presence/absence judging method implemented by the apparatus. FIG. 1 is a block diagram of the component presence/absence judging apparatus. FIG. 2 is a schematic view of an image pickup device in FIG. 1. It is to be noted that since there are plurality of boards whose images are to be taken, they are designated respectively as an ante-mounting board 13a, a post-mounting board 13b and an inspection board 13c. FIG. 3 shows a plan view of each board.

The component presence/absence judging apparatus 1 shown in FIG. 1 is an apparatus for judging whether or not components are mounted at predetermined places (i.e., scheduled or programmed target places) on a post-mounting operation board (i.e., inspection board) which has completed component mounting operations for mounting components at the predetermined places. Specifically, the apparatus 1 is an apparatus which beforehand acquires information from an ante-mounting board being a first reference board with no components mounted thereon and a post-mounting board being a second reference board with components mounted on predetermined places completely and correctly, the first and second reference boards being boards of the same kind, and which then judges whether or not the components are mounted on the predetermined places on each inspection board, based on the acquired information. Here, the "predetermined place" means a place at which a component is to be mounted on a board and more specifically, means a place at which the center of a component is to be located. The apparatus 1 is provided with an image pickup device 10 and a processing unit 11.

The image pickup device 10 is a device for relatively moving a board and a camera to successively pickup images of the predetermined portions on the board where components are to be mounted. Here, the "predetermined portion" means an area which covers either of a component and a place where the component is mounted, and a portion surrounding the component or the place. As shown in FIG. 2, the image pickup device 10 is provided with the camera 100, lateral or oblique illumination light sources 101, 102, a half mirror 103, and an epi-illumination light source 104.

The camera 100 is a device for picking up images of the upper surface of a board 13 on which components 12a, 12b are mounted as shown in FIGS. 2 and 3. Specifically, the image is picked up on each of the ante-mounting board 13a, the post-mounting board 13b and the inspection board 13c with each board being lighted up by the oblique illumination light sources 101, 102 and then, by the epi-illumination light source 104.

Each of the oblique illumination light sources 101, 102 is an illumination for lighting up the board 13 from obliquely above as indicated by the arrow in picking up an image by the camera 100. The oblique illumination light sources 101, 102 are arranged to throw lights toward the board 13 from obliquely above on one side and the other side.

The half mirror 103 is a plate-like member which reflects the light from the epi-illumination light source 104 so that the light from the epi-illumination light source 104 is normally lit on the board 13 from above as indicated by the arrow, and which enables the reflected light from the board 13 to reach the camera 100 therethrough. The half mirror 103 is arranged between the camera 100 and the board 13. Therefore, the camera 100 picks up an image of the board 13 which is lighted up by red light, green light and blue light radiated from the oblique illumination light sources 101, 102 and also picks up an image of the board 13 which is lighted up by white or natural light radiated from the epi-illumination light source 104.

The epi-illumination light source 104 is an illumination for normally throwing a light on the board 13 from above through the half mirror 103 as indicated by the arrow at a timing which differs from the timing when the oblique illumination light sources 101, 102 do, in picking up the image by the camera 100. The epi-illumination light source 104 is arranged to throw the light toward the half mirror 103.

The processing unit 11 is a device for processing the images picked up by the image pickup device 10 and for judging whether or not components are respectively mounted at predetermined places on a board. The processing unit 11 is composed of a CPU 110, a program memory 111 and a data memory 112. The CPU 110 processes the images picked up by the image pickup device 10 and judges the presence/absence of each component in accordance with a program stored in the program memory 111. As shown in FIG. 4, the processing unit 11 judges the presence/absence of each component through a registration step S1 and an inspection step S2 (component presence/absence judging method).

The registration step S1 is a preparation step executed prior to the inspection step S2. The registration step S1 is a step of determining an inspection area at each of predetermined portions where components are to be mounted, based on the images picked up by the image pickup device 10 and of acquiring and registering color information on the determined inspection area on the board before and after mounting operations. As shown in FIG. 5, the registration step S1 comprises an ante-mounting color information acquisition step S10 (ante-mounting color information acquisition means), a post-mounting color information acquisition step S11 (post-mounting color information acquisition means), an inspection area determination step S12 (inspection area determination means) and a storage step S13 (storage means).

Figure 6:
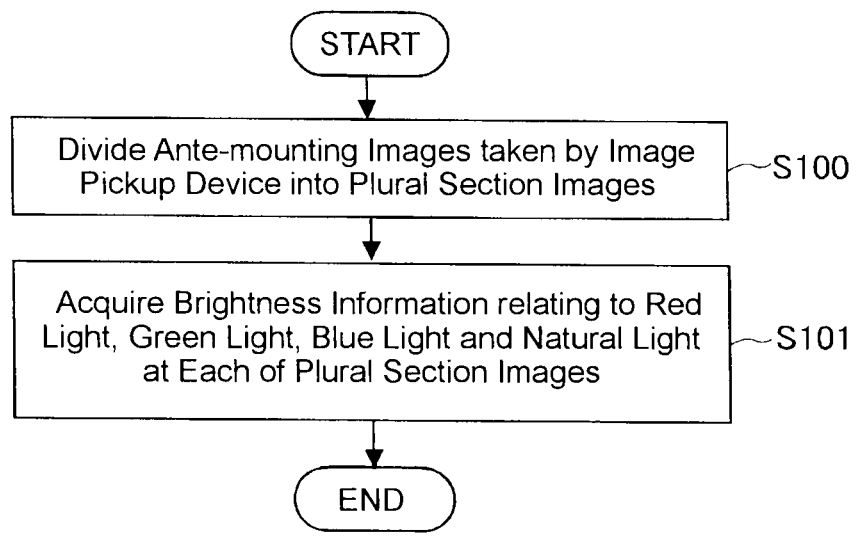
FIG. 6 is a flow chart showing an ante-mounting color information acquisition step in FIG. 5.

The ante-mounting color information acquisition step S10 is a step of acquiring ante-mounting color information from the ante-mounting images which the image pickup device 10 takes at each of predetermined portions each being a rectangular shape where components are to be mounted, on the ante-mounting board 13a before mounting the components at the predetermined places thereon. The image pickup device 10 shown in FIG. 2 relatively moves the ante-mounting board 13a and the camera 100 based on information which is set in advance as to the predetermined places where component are to be mounted. Then, the image pickup device 10 picks up ante-mounting images of each of the predetermined portions P1, P2 where components 12a, 12b are to be mounted, with each predetermined portion P1, P2 being lit first by the oblique illumination light sources 101, 102 and then by the epi-illumination light source 104. The ante-mounting color information can be acquired from the two ante-mounting images which are picked up by the image pickup device 10. Here, the ante-mounting board 13a is a first reference board which is used for the purpose of determining inspection areas and on which no component has been mounted at all though solder has been printed thereon. In this particular embodiment, description will be made taking as an example the board 13 on which two components 12a, 12b are to be mounted, as shown in FIG. 3. As shown in FIG. 6, the ante-mounting color information acquisition step S10 is composed of an image division step S100 (image division means) and a brightness information acquisition step S101 (brightness information acquisition means).

The image division step S100 is a step of equally dividing the respective ante-mounting images picked up by the image pickup device 10 into a plurality of predetermined section images. Specifically, as shown in FIGS. 7(A) and 7(B), each of the ante-mounting images of the predetermined portions P1, P2 on which the components 12a, 12b are to be mounted is equally divided into rectangular section images of 10×10. Each of the divided section images may be configured by one picture element or pixel or may be configured by many pixels.

The brightness information acquisition step S101 is a step of acquiring, as color information, brightness information relating to red light, green light, blue light and natural light which is made by blending all of red, green and blue lights, at each of the plural section images divided at the image division step S100. Each of the plural section images acquired as a result of dividing the ante-mounting image which is taken with the lights being thrown from the oblique illumination light sources 101, 102 shown in FIG. 2 is converted into respective color intensity images for red, green and blue, and brightness information on red light, green light and blue light is acquired as color information. Further, each of the plural section images acquired as a result of dividing the ante-mounting image which is taken with the light thrown from the epi-illumination light source 104 is converted into a natural light gray-scale image, and brightness information on the natural light is acquired as color information. As a result, with respect to each of the section images, four pieces of brightness information on red light, green light, blue light and natural light can be acquired as color information.

The post-mounting color information acquisition step S11 shown in FIG. 8 is a step of acquiring post-mounting color information from post-mounting images which the image pickup device 10 takes at each of the predetermined portions each being rectangular where components have been mounted, on the post-mounting board 13b which have mounted components at the predetermined places thereon. The image pickup device 10 shown in FIG. 2 relatively moves the post-mounting board 13b and the camera 100 based on information which is set in advance as to the predetermined places where component are mounted. Then, the image pickup device 10 picks up two post-mounting images of each of the predetermined portions P1, P2 where the components 12a, 12b have been mounted, with each predetermined portion P1, P2 being lit first by the oblique illumination light sources 101, 102 and then by the epi-illumination light source 104. The post-mounting color information can be acquired from the post-mounting images which are picked up by the image pickup device 10. Here, the post-mounting board 13b is a board which is used for the purpose of determining inspection areas and on which solder has been printed and all components have been mounted completely and correctly at the respective predetermined places. As shown in FIG. 8, the post-mounting color information acquisition step S11 is composed of an image division step S110 (image division means) and a brightness information acquisition step S111 (brightness information acquisition means).

The image division step S110 is a step of equally dividing the post-mounting images picked up by the image pickup device 10 into a plurality of section images in the same manner as is done at the image division step S100 shown in FIG. 6. Specifically, in the same manner as the image division step S100, each of the post-mounting images of the predetermined portions P1, P2 where the components 12a, 12b have been mounted is equally divided into rectangular section images of 10×10. The image division step S110 is the same as the image division step S100 though it only differs in images to be processed thereat.

The brightness information acquisition step S111 is a step of acquiring, as color information, brightness information relating to red light, green light, blue light and natural light in each of the plural section images divided at the image division step S110. The brightness information acquisition step S111 is the same as the brightness information acquisition step S101 shown in FIG. 6 though it only differs in images to be processed thereat.

The inspection area determination step S12 shown in FIG. 5 is a step of identifying a section (or sections on a certain occasion) having a large difference between the color information acquired from the ante-mounting images and the color information acquired from the post-mounting images, and of determining the identified section as an inspection section or area. As shown in FIG. 9, the inspection area determination step S12 is composed of a brightness difference information acquisition step S120 and a brightness difference information selection step S121.

The brightness difference information acquisition step S120 is a step of acquiring difference information between the brightness information on the section images of the ante-mounting images and the brightness information of the section images of the post-mounting images. Specifically, as brightness difference information, there is acquired difference information in brightness information on corresponding section images between the brightness information on the section images of the ante-mounting images acquired at the brightness information acquisition step S101 shown in FIG. 6 and the brightness information on the section images of the post-mounting images acquired at the brightness information acquisition step S111 shown in FIG. 8. Thus, four pieces of brightness difference information relating to red light, green light, blue light and natural light can be acquired for each one of the section images.

The brightness difference information selection step S121 is a step of selecting brightness difference information which meets a predetermined condition, from the acquired brightness difference information and of determining, as the inspection area, the area of a section image corresponding to the selected brightness difference information. Specifically, the four pieces of the brightness difference information acquired at the brightness difference information acquisition step S120 are added together to acquire total brightness difference information for each of the section images. Then, the areas of the section images which make a predetermined rate or percentage on the larger side in value of the acquired total brightness difference information are taken as inspection areas. In this particular embodiment, the area of a section image which becomes the largest in the value of the acquired total brightness difference information is taken as the inspection area. As a result, as shown in FIG. 7(A) for example, a section Ds1 at vertical address 4 and horizontal address 4 is selected as the inspection area for the predetermined portion P1 on which the component 12a is mounted. Further, as shown in FIG. 7(B) for example, a section Ds2 at vertical address 6 and horizontal address 8 is selected as the inspection area for the predetermined portion P2 on which the component 12b is mounted.

As shown in FIG. 10 in detail, the storage step 13 shown in FIG. 5 is a step of storing, for each of the predetermined portions, the inspection area having been determined at the inspection area determination step S12, the brightness information which is of the brightness information on the section images of the ante-mounting images acquired at the brightness information acquisition step S101 shown in FIG. 6 and which is on the section image corresponding to each inspection area, and the brightness information which is of the brightness information on the section images of the post-mounting images acquired at the brightness information acquisition step S111 shown in FIG. 8 and which is on the section image corresponding to each inspection area. Specifically, these data are stored in the data memory 112 shown in FIG. 1. As shown in FIGS. 7(A) and 7(B), the area Ds1 is stored as the inspection area for the predetermined portion P1 on which the component 12a is mounted, and the area Ds2 is stored as the inspection area for the predetermined portion P2 on which the component 12b is mounted. Of the brightness information of the section images acquired at the brightness information acquisition steps S101 and S111, the brightness information on the areas DS1, Ds2 is stored. This results in completing the registration step which is the preparation step executed prior to the inspection step S2.

The inspection step S2 shown in FIG. 4 is a step of acquiring the color information on each post-mounting operation board based on images picked up by the image pickup device 10 and of inspecting whether or not the components 12a, 12b are mounted at the predetermined places, based on the acquired color information after mounting operations, the inspection areas and the brightness information on the section images before and after the mounting operations which areas and information were stored at the storage step S13 shown in FIG. 5. As shown in FIG. 11, the inspection section S2 is composed of a post-mounting operation color information acquisition step S20 (post-mounting operation color information acquisition means) and a judgment step S21 (judgment means).

The post-mounting operation color information acquisition step S20 is a step executed on the inspection board 13c on which component mounting operations have been completed to mount components on the predetermined places thereon, for acquiring post-mounting operation color information from each inspection area on the post-mounting operation images which the image pickup device 10 takes at each of the predetermined portions of the rectangular shape each mounting a component thereon. The image pickup device 10 shown in FIG. 2 relatively moves the inspection board 13c and the camera 100 based on information which is set in advance as to the predetermined places where components are to be mounted. Then, the image pickup device 10 picks up two post-mounting operation images of each of the predetermined portions P1, P2 where components 12a, 12b have been mounted, with each predetermined portion P1, P2 being lit first by the oblique illumination light sources 101, 102 and then by the epi-illumination light source 104. The post-mounting operation color information can be acquired from the post-mounting operation images which are picked up by the image pickup device 10. Here, the inspection board 13c is a board to be inspected, on which solder has been printed and components have been mounted by mounting operations at the respective predetermined places. As shown in FIG. 12, the post-mounting operation color information acquisition step S20 is composed of an image division step S200 (image division means) and a brightness information acquisition step S201 (brightness information acquisition means).

The image division step S200 is a step of equally dividing the post-mounting operation images picked up by the image pickup device 10 into a plurality of section images, in the same manner as the image division step S100 shown in FIG. 6. Specifically, in the same manner as the image division step S100, each of the post-mounting operation images of the predetermined portions P1, P2 at which the components 12a, 12b have been mounted is equally divided into the rectangular section images of 10×10. The image division step S200 is the same in construction as the image division step S100 though it only differs in the images to be processed thereat.

The brightness information acquisition step S201 is a step of acquiring, as color information, brightness information relating to red light, green light, blue light and natural light from each of the plural section images divided at the image division step S200. The brightness information acquisition step S201 is the same in construction as the brightness information acquisition step S101 shown in FIG. 6 though it only differs in the images to be processed thereat.

The judgment step S21 shown in FIG. 13 is a step of judging whether or not the components 12a, 12b are mounted at the predetermined places on the board 13c, by comparing the post-mounting operation color information with the ante-mounting color information and the post-mounting color information. Specifically, the four pieces of the brightness information relating to the section image being each inspection area Ds1, Ds2 on the inspection board 13c are compared with the respective four pieces of the brightness information relating to the respective section images being the corresponding inspection area Ds1, Ds2 on the ante-mounting board 13a and the post-mounting board 13b, and judgment of whether or not the component is mounted at each of the predetermined places on each inspection board 13c is made in dependence on which of the brightness information on the ante-mounting board 13a and the brightness information on the post-mounting board 13b is closer to the brightness information on the post-mounting operation board 13c in the four scales (i.e., red, green, blue and natural colors) of comparison (S210-S213). When the four pieces of brightness information on the section image of each inspection area Ds1, Ds2 on the inspection board 13c are closer to the four pieces of brightness information on the section image of each inspection area Ds1, Ds2 on the post-mounting board 13b, it is judged that the component 12a, 12b is present at each such predetermined place on the inspection board 13c (S212). On the contrary, when the four pieces of brightness information on the section image of each inspection area Ds1, Ds2 on the inspection board 13c are closer to the four pieces of brightness information on the section image of each inspection area Ds1, Ds2 on the ante-mounting board 13a, it is judged that the component 12a, 12b is absent at each such predetermined place on the inspection board 13c (S213).

Next, advantages will be described. According to the present embodiment, the section which has a large difference in color information before and after the mounting of each component is determined as the inspection area. Then, judgment of whether or not each component is mounted is made in dependence on the color information on the inspection area. Therefore, whether or not a component is mounted can be judged accurately in comparison with the prior art wherein such judgment is made in dependence on the color information at around the center part of each component.

Further, according to the present embodiment, the image picked up by the image pickup device 10 is divided into the plurality of section images at the inspection area determination step S12. Then, the section image which has a big change in the brightness information is specified and is determined as the inspection area. Therefore, it is possible to reliably determine as the inspection area the section where the difference in the color information is large between the ante-mounting board 13a and the post-mounting board 13b.

Further, according to the present embodiment, at each of the brightness information acquisition steps S101, S111 and S201, it is possible to acquire the brightness information relating to red light, green light, blue light and natural light which is made by blending all of these lights, with respect to each of the plural divided section images. Therefore, it is possible to reliably acquire the brightness information.

Additionally, according to the present embodiment, lights are thrown onto the board 13 by using the oblique illumination light sources 101, 102 and the epi-illumination light source 104. By the oblique illumination light sources 101, 102 which throw lights from obliquely above, it is possible to reliably acquire the brightness information relating to red light, green light and blue light. Further, by the epi-illumination light source 104 which throws light normally from above, it is possible to reliably acquire the brightness information relating to natural light. Therefore, the color information can be acquired reliably.

Although the present embodiment takes an example that acquires the post-mounting color information from the post-mounting images at the post-mounting color information acquisition step S11, the present invention is not limited to doing so. For example, where numerals, marks and the like are written on the surface of a component, it is possible to prepare an average picture image from a post-mounting image and an image to which the post-mounting image is turned through an angle of 180 degrees, and to use the average picture image as the post-mounting image. This makes it possible to suppress to the utmost error judgments which would otherwise be caused by the numerals, marks or the like which are written on the surface of the component. The method in this modified form can be wide applied to the image processing for components without being limited to judgment as to the presence/absence of a component.

Further, although the present embodiment takes an example that, at the brightness difference information acquisition step S120, uses the section images of 10×10 into which the rectangular image is divided, the present invention is not limited to doing so. For example, of the section images of 10×10, section images of 8×8 which are left as a result of excluding those at the peripheral parts may be chosen to acquire the brightness difference information therefrom. By doing so, it becomes possible to eliminate influences which are caused by other images included at the peripheral parts than components. Further, the section image areas used may be altered in dependence on the dimension and shape of components. The method in this modified form can be wide applied to the image processing for components without being limited to judgment as to the presence/absence of a component.

Further, although the present embodiment takes an example that, at the brightness difference information selection step S121, determines as inspection areas the areas of section images included in the predetermined percentages or rates which are on the larger side in value of the total brightness difference information, the present invention is not limited to doing so. The inspection areas may be taken as the areas of plural section images each having the acquired total brightness difference information whose value is equal to or greater than a predetermined threshold value. Further, the inspection area is taken as the area of a section image which has the total brightness difference information being the largest.

Furthermore, although the present embodiment takes an example that, at each of the brightness information acquisition steps S101, S111, S201, uses the oblique illumination light sources 101, 102 and the epi-illumination light source 104 and acquires the brightness information relating to red light, green light, blue light and natural light which is made by blending all of these lights, the present invention is not limited to doing so. For example, the oblique illumination light sources only may be used. It is sufficient if there can be acquired brightness information relating to at least two lights of red light, green light, blue light and the light made by blending these lights. In each of these modified forms, it is possible to attain the same advantageous effects.

Further, although the present embodiment takes an example that the ante-mounting board 13a and the post-mounting board 13b are boards of the same kind but are completely different boards, the present invention is not limited to such an example. After the execution of the ante-mounting color information acquisition step S10, the ante-mounting board 13a may be used as the post-mounting board 13b by having all of components mounted at predetermined places completely and correctly.

Further, although the present embodiment takes an example that each of the brightness information acquisition steps S101, S111 acquires the brightness information relating to red light, green light, blue light and natural light, that is, four lights on each of the plural section images and that the inspection area determination step S12 determines the inspection area based on the brightness information relating to the four lights acquired at each of the brightness information acquisition steps S101, S111, the present invention is not limited to doing so. It is possible to determine the inspection area by acquiring the brightness information relating to at least two lights.

Further, although the inspection step S2 is executed after the execution of the registration step S1, the present invention is not limited to executing the inspection step S2 each time an inspection board to be inspected is made up by completing the mountings of components on a board 13. The inspection steps may be executed in succession after a plurality of inspection boards 13c are made up.

In addition, the present embodiment takes an example that the brightness information relating to red light, green light and blue light is acquired from the lights from the two oblique illumination light sources 101, 102 while the brightness information relating to natural light is acquired from the one epi-illumination light source 104, the present invention is not limited to doing so. There may be one oblique illumination light source only. Further, the brightness information relating to natural light may be acquired from the light from the oblique illumination light source.

Various features and many of the attendant advantages in the foregoing embodiment will be summarized as follows:

In the component presence/absence judging apparatus and the method in the embodiment typically shown in FIGS. 3, 7(A), 7(B), 9 and 13, the section Ds1, Ds2 having a larger difference in color information between before and after the mounting of the component 12a, 12b is determined as the inspection area (S121). Then, whether or not the component 12a, 12b is mounted is judged in dependence on the color information in the inspection area (S211). Thus, judgment of whether or not the component 12a, 12b is mounted can be made accurately in comparison with the prior art wherein such judgment is made in dependence on the color information at around the center part of a component.

Also in the component presence/absence judging apparatus and method in the embodiment typically shown in FIGS. 2, 3, 6, 7(A), 7(B), 8 and 9, each of the images picked up by the image pickup device 10 is divided into the plurality of section images (S100, S110). Then, the section Ds1, Ds2 which has a large difference in brightness information between the ante and post-mounting images is indentified to be determined as the inspection area for the predetermined portion P1, P2 (S121). Therefore, it is possible to reliably determine as the inspection area the section Ds1, Ds2 whose color information is large in difference between the ante and post-mounting images.

Also in the component presence/absence judging apparatus in the embodiment typically shown in FIGS. 2 and 3, the image pickup device 10 is provided with the oblique illumination light source 101 (or 102) for lighting up the boards 13a, 13b, 13c from obliquely above and the epi-illumination light source 104 for lighting up the boards 13a, 13b, 13c normally from above. The image of the predetermined portion P1, P2 on each board 13 is picked up while being lit by the oblique illumination light sources 101 (or 102) and is picked up while being lit by the epi-illumination light source 104. Therefore, it is possible to reliably acquire the color information.

Obviously, numerous further modifications and variations of the present invention are possible in light of the above teachings. It is therefore to be understood that within the scope of the appended claims, the present invention may be practiced otherwise than as specifically described herein.

What is claimed is:

1. A component presence/absence judging apparatus for judging whether or not a component is mounted at a predetermined place on a board after a component mounting operation that mounts the component on the board, the apparatus comprising:
   an image pickup device for relatively moving the board and a camera to pick up an image of a predetermined portion on the board where the component is to be mounted; and
   circuitry configured to:
   acquire ante-mounting color information from an ante-mounting image that the camera picks up at a predetermined portion on an ante-mounting board before mounting the component at the predetermined place;
   acquire post-mounting color information from a post-mounting image that the camera picks up at a predetermined portion on a post-mounting board after mounting the component at the predetermined place;
   determine an inspection area by identifying a section having a large difference between the ante-mounting color information and the post-mounting color information, and by identifying a section image having a large difference between brightness information on at least two lights at each of the section images of the ante-mounting image and brightness information on at least two lights at each of the section images of the post-mounting image that respectively correspond to section images of the ante-mounting image;
   store, in a memory, for each predetermined portion, the inspection area, the ante-mounting color information, and the post-mounting color information in the inspection area;
   acquire post-mounting operation color information from the inspection area on a post-mounting operation image that the camera picks up at a predetermined portion on an inspection board after the component mounting operation; and
   judge whether or not the component is mounted at a predetermined place on the inspection board, by comparing the post-mounting operation color information with the ante-mounting color information and the post-mounting color information.

2. The component presence/absence judging apparatus as set forth in claim 1, wherein the circuitry is further configured to:
   divide a corresponding one of the ante-mounting image, the post-mounting image, and the post-mounting operation image into a plurality of section images having a predetermined number of divisions; and
   acquire as the color information brightness information relating to at least two lights of red light, green light, blue light, and a light which is made by blending all of these lights, at each of the divided plurality of section images.

3. The component presence/absence judging apparatus as set forth in claim 1, wherein the image pickup device comprises:
   an oblique illumination light source for lighting up the boards from obliquely above; and
   an epi-illumination light source for lighting up the boards normally from above; and
   wherein the image pickup device is configured to pick up an image at the predetermined portion on each of the boards being lit by the oblique illumination light source and to pick up an image at the predetermined portion on each of the boards being lit by the epi-illumination light source.

4. A component presence/absence judging method for judging whether or not a component is mounted at a predetermined place on a board after a component mounting operation that mounts the component on the board, the method comprising:

acquiring, using circuitry, ante-mounting color information from an ante-mounting image that an image pickup device picks up at a predetermined portion, where the component is to be mounted, on an ante-mounting board before mounting the component at a predetermined place;

acquiring, using the circuitry, post-mounting color information from a post-mounting image that the image pickup device picks up at a predetermined portion on a post-mounting board after mounting the component at the predetermined place;

determining, using the circuitry, an inspection area by identifying a section having a large difference between the ante-mounting color information and the post-mounting color information, and by identifying a section image having a large difference between brightness information on at least two lights at each of the section images of the ante-mounting image and brightness information on at least two lights at each of the section images of the post-mounting image that respectively correspond to section images of the ante-mounting image;

storing in a memory, using the circuitry, for each predetermined portion, the inspection area, the ante-mounting color information, and the post-mounting color information in the inspection area;

acquiring, using the circuitry, post-mounting operation color information from the inspection area on a post-mounting operation image that the camera picks up at a predetermined portion on an inspection board after the component mounting operation; and judging, using the circuitry, whether or not the component is mounted at a predetermined place on the inspection board, by comparing the post-mounting operation color information with the ante-mounting color information and the post-mounting color information.

5. The component presence/absence judging method as set forth in claim 4, further comprising:

dividing, using the circuitry, a corresponding one of the ante-mounting image, the post-mounting image, and the post-mounting operation image into a plurality of section images having a predetermined number of divisions; and acquiring, using the circuitry, as the color information brightness information relating to at least two lights of red light, green light, blue light and a light which is made by blending all of these lights, at each of the divided plurality of section images.

* * * * *